United States Patent [19]

Borah et al.

[11] Patent Number: 4,789,235

[45] Date of Patent: Dec. 6, 1988

[54] METHOD AND SYSTEM FOR GENERATING A DESCRIPTION OF THE DISTRIBUTION OF LOOKING TIME AS PEOPLE WATCH TELEVISION COMMERCIALS

[75] Inventors: Joshau D. Borah, Winchester, Mass.; Barbara N. Flagg, Bellport, N.Y.

[73] Assignee: Applied Science Group, Inc., Waltham, Mass.

[21] Appl. No.: 166,776

[22] Filed: Mar. 7, 1988

Related U.S. Application Data

[63] Continuation of Ser. No. 848,154, Apr. 4, 1986, abandoned.

[51] Int. Cl.[4] ............................ A61B 3/14; A61B 3/00
[52] U.S. Cl. ...................................... 351/246; 351/210
[58] Field of Search .......................................... 351/246

[56] References Cited

PUBLICATIONS

Eye-Trac Catalog by ASL, Copyright 1982.

Primary Examiner—Rodney B. Bovernick
Assistant Examiner—Jay Ryan
Attorney, Agent, or Firm—Body, Vickers & Daniels

[57] ABSTRACT

A mean distribution of viewer looking time for a group of individuals each viewing a dynamic audio and visual video program measures the mean attention span corresponding to each distinct audio and video component of the overall program. The video program is recorded in measured sequential scenes, with each scene corresponding to a selected audio or visual signal and being comprised of distinct visual areas of interest. Eye point of gaze data is recorded for the duration of the program for each individual viewer in the group. A compiled eye point of gaze data file is compared with a scene by scene data file to produce a third data file showing a mean distribution of viewer looking time for each selected audio and visual signal.

6 Claims, 9 Drawing Sheets

NOT AOI     = .73%
AOI (1)     = 55.46%
AOI (2)     = 43.80%
AOI (4)+(2) = 99.26%

$d = K \sin \theta$

METHOD AND SYSTEM FOR GENERATING A DESCRIPTION OF THE DISTRIBUTION OF LOOKING TIME AS PEOPLE WATCH TELEVISION COMMERCIALS

This is a continuation, of Ser. No. 848,154 filed Apr. 4, 1986, now abandoned.

The present invention relates to the art of evaluating television commercials and more particularly to a method and apparatus for generating a description of the distribution of looking time as people watch television commercials, which distributions are indicative of the actual looking time for known objects in commercials with varying scenes.

Incorporation by Reference

As background information the following publications are incorporated by reference: Semiautomatic Eye Movement Data Analysis Techniques for Experiments with Varying Scenes, David Sheena and Barbara N. Flagg, Eye Movements and the High Physchological Functions, 1978, Publisher Lawrence Erlbaum, Eye Movements - Cognition and Visual Perceptions, 1981, Publisher Lawrence Erlbaum, pages 257-268: Eye-Movement Measurement Techniques, Lawrence R. Young, David Sheena, American Psychologist, Vol. 30, No. 3, March 1975, pages 315-329: Methods & Design Survey of Eye Movement Recording Methods, Behavior Research Methods & Instrumentation, 1975, Vol. 7(5), pages 397-429: eye-trac catalog by ASL, copyright 1982. The prior publications disclose two technical areas involved in the present invention and are incorporated as prior art and as known information which is not repeated in detail in this specification. There is no intent to imply interrelationship of these separate technical dissertations.

BACKGROUND

For many years efforts have been expended to analyze the visual significance of commercials and advertising copy of the static type, such as newspaper print, and the dynamic type, such as television commercials. Originally, evaluations and correlated advertising techniques were performed by persons considered to have highly developed skills or artistic abilities. This personalized evaluation technique has continued. Advertising and commercial analysis and evaluation is often performed by staff personnel or independent consultants employed by various advertising agencies and publication houses for evaluating the visual impact of their work product. The basic difficulty with this subjective, artistic technique is that the evaluation changes with the person making the evaluation. To overcome this disadvantage, many publishers and advertising agencies have developed elaborate interviewing and panel discussion groups for the purpose of evaluating advertising material. The advertising material is shown to individuals, separately or in groups. Discussions are conducted on the impact and impressions regarding the various advertising concepts. This group session technique is still widely used: however, it is extremely expensive, somewhat unreliable and wrought with inaccuracies due to the bias of the analysis program and the natural psychological tendency of persons to respond in a manner believed to be sought by the interviewer, as opposed to objective responses. Even though the interviews and panel discission type of advertising analysis is known to have certain drawbacks, such as expense and suspected reliability, the techniques are still employed due to a complete lack of a replacement by an objective technique for advertising evaluation. This is the basic problem addressed by the present invention and is the factual background of the art to which the present invention is directed. The present invention is a distinct and recognizable improvement in media analysis techniques.

Turning now to another background matter, in the mid 1960's there was developed eye monitoring equipment which could be used to detect the size of the pupil of an individual, the movement of the eye, and the eye point of gaze as a function of time. These locations were oriented with respect to a fixed head of an individual. The fixed head position was assured by a headrest or chin rest. The most popular and original eye movement detecting concept was the limbus eye monitor as shown in Young U.S. Pat. No. 3,473,868. These devices advanced through various improvements and modifications which are illustrated in the United States Letters Patent Newman U.S. Pat. No. 3,583,794; Feather U.S. Pat. No. 3,594,072; Millodot U.S. Pat. No. 3,623,799; Newman U.S. Pat. No. 3,679,295; and Young U.S. Pat. No. 3,689,135. Various eye movement instruments and techniques of using them are disclosed in the publications incorporated by reference herein for the purposes of background information. The most advanced technique now used in eye monitoring is the corneal-reflection, pupil center techniques wherein the position of the eye is determined by the displacement of the corneal reflection from the pupil center By using a coaxial video camera and light source, the pupil center appears bright to the camera and the reflection i This technique is now being used in the most advanced eye movement monitor sold by Applied Science Laboratories of Waltham, Massachusetts under the designation of No. 1998.

Eye monitor equipment available since the 1960's has not been useful for advertisement analysis for a variety of reasons. The information obtained by using early eye monitors was not considered to be an accurate and repeatable evaluation of visual advertising material. Further, the early eye monitoring equipment required a chin rest or head restraints, distractive glasses and highly visible equipment which would distract substantially from an individual's normal evaluation of printed material. Indeed, much of the eye monitoring equipment could not be used by persons requiring corrective eyewear, such as spectacles or contact lenses. For that reason alone, the demographics of eye monitor evaluation were not consistent with the general population. Distractions and technical limitations were believed to impose such restrictions that eye monitoring for the purposes of evaluating visual advertising material was at best a technical oddity. A few companies did initiate an evaluation of stationary print material by available eye monitors. These companies did not have the sophisticated computer hardware and software to analyze eye movements in relation to moving scenes. Clearly, before the present invention, there was no practical way known to the advertising agencies and publishers for using eye monitors for the purposes of evaluating constantly moving and changing visual scenes, such as experienced in television commercials, without obtrusive visual and physical distractions. Television commercials, to which this invention is directed, not only include constantly changing visual scenes to be processed by a viewer, but also have an overlay of audio signals containing concepts intended to influence the visual image being processed at any given time. Television commercials with interplay of video and audio programming presented such horrendous, massive information sources that intelligent machine readable data were believed to be unobtainable, at least for acceptable equipment and analysis costs. For that reason, eye monitors were, until the present invention, limited to evaluations of static type advertising material in an economic fashion needed for commercial acceptance. For these reasons, the art to which the present invention is directed, even considering the existing eye monitoring equipment, did not overcome and/or replace, even partially, the interview and panel discussion type evaluation of television commercials. Even with the advent of such highly computerized eye movement equipment, such as the new model No. 1998 eye view monitor systems, these systems had no data recording or analysis software making them useful or used in evaluation of television commercials. Even with the use of some type of stop scene input information, it was not known how eye movements could be related to rapidly moving and changing combined audio and video television commercials in a manner resulting in commercially viable, repeatable television commercial evaluations.

THE INVENTION

The present invention relates to a system and method of evaluating television commercials with a selected, but limited amount of information, which information is indicative of an accurate and repeatable evaluation of the audio-visual commercial. Readily available equipment is employed in a novel combination to render commercially feasible, objective television commercial analysis using untrained subjects demographically correlated with the television viewing public.

In accordance with the present invention there is provided a method of generating a distribution of actual looking time for a television commercial containing a video signal and a synchronized audio signal where both signals are recorded for real time playback on a television monitor. The distribution of actual looking time is the time during which an individual is looking at a particular position on a visual plane and is indicative of the visual impact of a certain object in the television commercial and the interplay between the various objects and the audio signal attempting to influence the distribution of actual looking time on a continuous basis as the commercial is being played. This looking time, when using the present invention, is devoid of psychological and personal bias and background and is obtained by a manageable amount of data which can be analyzed to obtain looking time.

The method in accordance with the present invention involves displaying the television commercial to an individual in a visually neutral room by way of a television monitor in the room. The term "visually neutral" indicates that the individual watches the television commercial in the same way that he would view a television commercial in a real life situation. There are no obtrusive cameras, lights and technical equipment in the room which would in any way influence the eye movement of the individual or the psychological concentration and perception of the individual. Such a neutral room does not involve any head supports, chin rests or goggles which would destroy the visual neutrality of the room in which the measurements are being made. In this manner, the eye movement measurements being made in accordance with the new method are, to the best extent possible, involuntary and psychologically objective if not also physiologically repeatable. Without such a neutral room, extraneous distraction can occur which would affect distribution of actual looking time for the television commercial being shown to the individual in the real time mode on the monitor in the neutral room.

The method of the present invention further involves detecting the position of the eye of the selected individual at preselected time base intervals by way of a pupil center and corneal reflection eye monitor wherein the intervals are substantially less than about 1/30 of a second. By recording the position of the eyes each 1/30 of a second or faster, eye positions can be detected and, in accordance with the new method, these detected eye positions can be reduced to a series of fixations each having parameters, such as a starting time, duration and x,y coordinates with respect to the video display. These individual fixation parameters are then recorded in a storage file as a set of fixations which are synchronized with the television commercial including both the visual and audio aspects. In this manner, a large amount of eye position data are reduced to a smaller amount of manageable data in the form of a series of fixations, requiring a minimum of data capacity. In the preferred embodiment, the real time base intervals are approximately 1/60 of a second, which spacing will provide necessary temporal information to identify each fixation and its duration, since fixations by humans have a duration no less than about 0.1 seconds. Consequently, fixations of the minimum length will encompass at least 6 data samples. If the x,y coordinates of at least 6 sequential data samples do not vary substantially, a fixation is recognized and stored with or by its parameters.

In accordance with still a further continuing aspect of the present invention, the television commercial is divided into a series of scenes each having a real time duration and each made up of known areas of interest with boundaries defined by a set of x,y coordinates for each area of interest for each scene. Preferably, the x,y coordinates for each area of interest define a rectangle in the scene shown on a television monitor. As is known, the frame of the television commercial changes each 1/30 of a second. The real time duration for any given scene in accordance with the invention is the length of time, i.e. number of frames, in which the various selected areas of interest do not substantially change in their x,y coordinates or content. Thus, in a television commercial a scene will have a starting time and duration during which the areas of interest are generally the same. In this manner the areas of interest remain "valid", i.e. continue to circumscribe and include a selected visual image or concept, for a given scene. Indeed, the duration of a scene, in time or frames, is set to be as long as the areas of interest remain valid. In addition, a scene duration can be determined when an audio message has been completed. For instance, one scene will have a certain part of an audio signal. Consequently, a scene can be changed or stopped for analysis purposes by either a substantial change in the x,y coordinates for an area of interest in the scene, such as a drastically moving object, or by a change in the audio concept for the scene. The scenes are then recorded on a data file by scene parameters, i.e. number or label, its starting time, its duration, and the fixed coordinates of the various areas of interest in the scene during the total scene duration. This scene data or storage file is then compared to the fixation storage file for a specific individual to produce a third data file specifying the area of interest associated with each fixation in each scene of the television commerical. After repeating this process or method for various individuals using the same scene data file with each individual fixation file, a group data file is produced specifying the mean distribution of looking time for each area of interest for each scene over the entire sample of subjects. The number of individuals selected for viewing is determined by demographic techniques of selection and forms no part of the invention except to the extent that more than one individual is tested. The group data file of looking time can be displayed in various forms. This is the end product obtainable only by the present invention in an economical and accurate manner. The group data file contains highly objective information indicating the distribution of actual looking time for a television commercial and overcomes all of the disadvantages of prior attempts to evaluate, from an objectively pure standpoint,the viewer's visual response to television commercials.

By using this concept of reducing the number of scenes into areas of interest which are synchronized with the video and audio signals, it is possible to use the fixation points and the saccades between the fixations to reduce a substantial amount of digital information which is a byproduct of the invention and allows a massive amount of information to be utilized without overloading a normal computer available for evaluating the output of a commercially available computer based eye view monitor system. Only by reducing the amount of data and selecting the essential data as indicated in accordance with the invention can the television commercial be analyzed in a practical fashion.

The primary object of the present invention is the provision of a method and system which can be used economically for analyzing the viewing behavior in response to a television commercial having changing scenes. By the present invention, commercial analysis of television commercials is possible. This analysis is objective and does not require the massive computers of research and academic facilities.

Still a further object of the present invention is the provision of a method and system, as defined above, which system minimizes the necessary data essential for objective evaluation of television commercials.

Still a further object of the present invention is the provision of a method and system, as defined above, which method and system utilize a visually neutral room wherein there are no obtrusive, distracting appurtenances and wherein it is not necessary to attach or associate equipment with the person or individual from whom the viewing behavior is obtained.

Still a further object of the present invention is the provision of a method and above, which method and system employ eye movement monitors compatible with many people having contact lenses or spectacles so that the demographic sampling can be more universal.

Still a further object of the present invention is the provision of a method and system, as defined above, which method and system employ techniques for minimizing the amount of data required to evaluate television commercials.

Yet another object of the present invention is the provision of a method and system, as defined above, which method and system employ primarily fixations having computer durations and locations within a scene for the purposes of obtaining television commercial analyzing data, such as distribution of looking time for the several sequentially displayed scenes.

The present invention is used as an advertising research service which uses eye movement monitoring along with immediate recall data as tools to aid in evaluating the effectiveness of television commercials. Much prior research determines what information is actually remembered from a television commercial. This information is obtained by interviews after viewing of a commercial. Little emphasis has heretofore been placed, however, on how the information is extracted by an individual from a television commercial or why communication goals have or have not been realized with a particular television commercial. After the fact research methods are limited because they do not tell what in the television presentation is actually affecting the achievement of the commercial's ultimate marketing goals. This information is obtainable by, and is a major object of, using the present invention to record the viewer's moment-to-moment response to a commercial, while the viewer is actually watching a particular television commercial. This novel marketing analysis concept is done by monitoring the viewer's eye movement pattern to obtain the actual distribution of the viewer's attention while they are watching the commercial. This concept is the essence of the invention and produces information only by employing the present invention and not obtainable by other commercial evaluating techniques, whether using eye movement monitoring equipment or not. The object of the present invention is obtaining this tremendously advantageous by using equipment available at a reasonable cost to normal commercial establishments.

Television is perceived and understood as a moving and changing mosaic presentation of various images and sounds. Eye movement data provided by the present invention provide an objective continuous record of the interaction between the elements of the television presentation, both video and audio, and the viewer's visual behavior during the presentation. Data obtained economically by the present invention through the periodic recording of eye movements produce an end result which is a diagnostic tool for advertisers available as an adjunct to evaluating a given television commercial. This new evaluation tool produced by employing the present invention may be an accurate, dependable distribution of actual looking time over various areas of interest for a given scene. This information is an end result of using the invention and is an end product obtainable by employing the present invention. The manner in which this information is employed can be varied. It is very useful for the purpose of revising television commercials to improve the visual impact. Viewing pattern data coupled with post-viewing, immediate recall gives a comprehensive picture of the processing of a television commercial by viewers. The present invention relates to one aspect of that process, which aspect is an end result in itself and is a diagnostic tool extremely valuable in the overall analysis of a television commercial from a scene by scene standpoint. Since the use of the present invention gives accurate distribution of looking at various objects in the many scenes in a neutral environment, advertisers can and will place confidence in the results, which results are used by marketing agencies to improve and then sell the commercial to a client or advertiser. This advantage has not been available to agencies at any cost before the present invention.

In appreciation of the present invention, it is realized that human eyes constantly move to select and process visual information. The eyes stop and move over a visual scene at the average rate of three times per second. The sampling rate employed in the present invention is twenty times higher than normal fixation rate. The point at which the viewer's eyes stop to process visual information is called the "fixation". The movement of the eye is made between fixations and is called the "saccade". In accordance with the present invention, the fixations are computed since they are indicative of the actual intake and assimilation of visual information. The position and duration of the eye fixations reflect continuous processing of a visual display. The significance of this concept for television advertising research is extremely important and is mentioned here as background information for evaluating the present invention, since the visual sense is the primary sensory mode for mentally processing data from television commercials. One purpose of the audio portion of the commercial is to emphasize or de-emphasize aspects of the video presentation, and the audio portion may be instrumental in influencing the pattern of fixations as the subject views the television commercial.

The present invention employs computer processing which may be varied as long as the information obtainable by the present invention is obtained in any of a number of algorithmic processes. The data obtained by the invention are highly accurate and reliable for indicating and recording the position on the television screen at which the viewer is looking at any given time. The analysis software is only employed for extracting the fixations from the data as obtained by the present invention and converting them into starting times and durations expressed as frames or seconds, together with two-dimensional locations. The use of fixation measurements reduces the data needed in practicing the invention. The fixation information obtained by the present invention is employed for generating several viewing quantities which quantities are the end result obtainable by employing the present invention. The primary outcome of the present invention is the production of sufficient information to obtain a distribution of looking time, indicating as to each separate and distinct scene, the various different areas of interest and the mean amount of time employed by a sample of people in fixating each of the areas of interest in each scene.

As a byproduct, the location and designation of separate and distinct time spaced fixations can be employed for the purposes of determining the "scanning activity" for a particular scene. For instance, if a large number of fixations occur in a scene over a short period of time, this is indicative of a very active scanning process by the eye. If there are relatively few fixations, there is an inactive scanning process being performed which inactivity could be indicative of disinterest in, or over the length of, a particular scene of a television commercial and a weakness in the visual presentation of this scene. This determination is obtainable by the outcome of the present invention, which invention develops the tool locating the various fixations of the eye over a given real time base and synchronized with the time base of the television commercial being evaluated. This general outline of the invention and its attributes, when placed in the context of the background of the information, is employed for the purposes of realizing still further the objects and advantages of the present invention.

The present invention obtains the actual eye point of gaze of a sample of people for a given scene and the obtained data are processed in accordance with standard practice to obtain locations and durations of fixation and saccades at various points in time. From these fixations, a variety of information can be calculated which is not part of the present invention. One result of the present invention is a physical and temporal distribution of fixations over a scene. From this information, the scanning activity and other information can be obtained.

In the past, the volume of data collected by eye movement monitoring systems was time consuming and cumbersome to analyze. The present automated software which is part of the invention reduces the data sufficiently to make quantitative analysis possible on a commercial scale. The present invention first exposes the people being tested to a normal visual environment which does not contain extraneous distractions which would influence eye movement patterns. The light source used in the present invention is coaxial with the camera monitoring the corneal reflection and pupil: therefore, the pupil appears bright which produces better contrast for the purpose of detection by the circuitry and computer used in known eye movement monitors. A servo-operated mirror enables the system to accurately follow head movement. This equipment used in the present invention includes tracking of the head as it moves. The head does not need physical restraints. In this manner there is no physical interference and dynamic scenes can be analyzed with consistent results.

The present invention measures and records data regarding point of gaze of a person's eye as a function of time for a preselected outlined scene. These data are reduced to a series of fixations which are matched with the visual elements in the scene and for the time during which the scene exists. This information is sufficient to obtain data necessary for analyzing a television commercial when used in connection with, or without, companion interviews of the people being processed in accordance with the present invention.

These objects and advantages and the discussed attributes of the present invention, and others, are obtained and will become apparent from the following description taken together with the accompanying drawings which are described in the following section.

Figure 1:
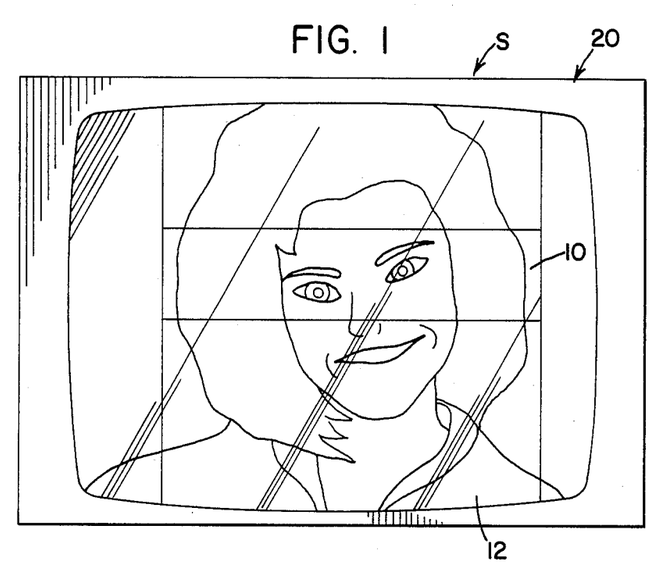
FIG. 1 is a view of a single scene from a television commercial, with certain areas of interest defined by boxes or rectangles in accordance with the common scene processing used in the present invention.
Figure 2:
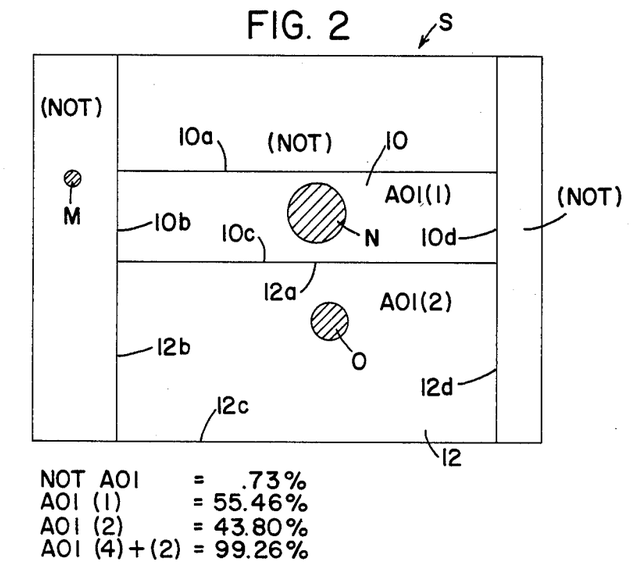
FIG. 2 is a view similar to FIG. 1 with details of the area of interest and indicators of distribution of looking time obtained in practice by use of the present invention.

Referring now to the drawings wherein the showings are for the purpose of illustrating the preferred embodiment of the invention used to perform the functions previously described as accomplished by the present invention, FIGS. 1 and 2 illustrate a scene S of which there are a finite number in a television commercial. Scene S is divided into two specific areas of interest, i.e. area of interest 10 including the eyes of a woman and area of interest 12 including the neck and mouth of the same woman. The areas of the scene S not circumscribed by areas of interest 10 and 12 are referred to as Not AOI in FIG. 2. This scene from an actual television commercial remains the same until the areas of interest 10, 12 change from the coordinates defining a box made up of lines 10a–10d and 12a–12d, as best shown in FIG. 2.

Figure 14:
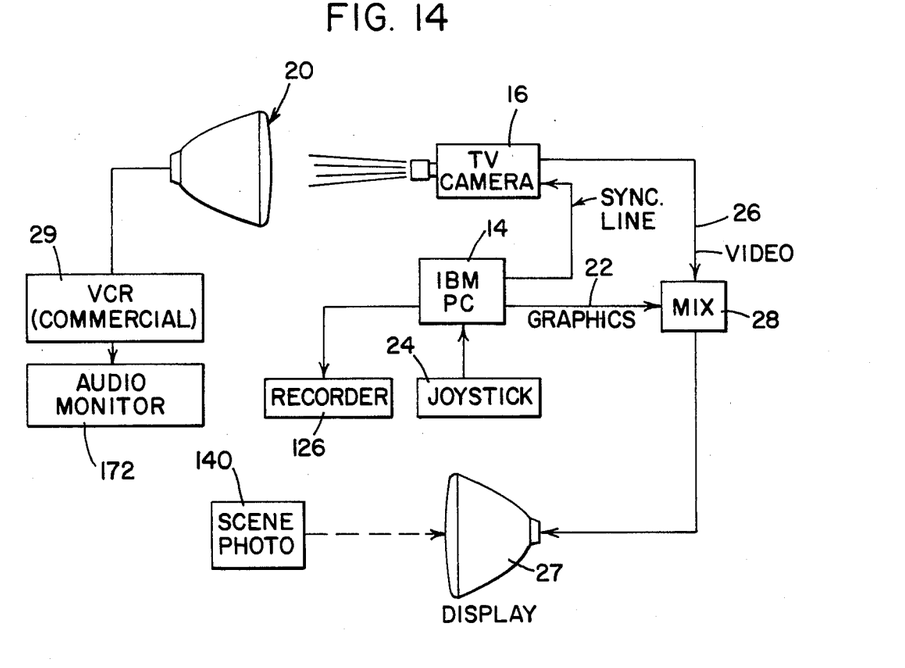

The coordinates of these boxes are fixed for a given scene and as long as the eyes of the woman stay in the area of interest 10 and the lower portion of the woman does not change, the scene S has the same architecture and is a single scene. In this manner, a television commercial can be divided into a discrete, limited number of scenes having a starting time and duration which can be recorded and then processed, as by a computer. The scene continues and has a duration in frames or time until the areas of interest (AOI's) are no longer valid. This could happen by moving the woman or changing to another subject. In accordance with one aspect of the invention, the television commercial displayed on television monitor 20 is divided into a series of scenes S having generally fixed areas of interest (AOI's) lasting for a finite time (number of frames) or duration. The next scene may occur when the AOI's are no longer valid, such as when the camera is withdrawn from the woman so that the eyes then appear in a different position on the television monitor 20. A different scene having different architecture of boxes (AOI's) follows scene S. These boxes, defining the AOI's for a given scene, can be created by the aid of a joystick and graphics software shown in FIG. 14. The AOI's for a given scene may be displayed over that scene in the television commercial. The need for a next scene is determined, and new AOI's are constructed by the graphics system. This procedure is repeated for the whole commercial. This process is illustrated in FIG. 14 wherein the joystick controls an IBM personal computer which synchronizes the monitor 20. The graphics created and directed to line 22 are obtained by the IBM PC 14 operating in conjunction with the joystick 24. The television picture is obtained from the television camera 16 and is synchronized by signal on line from IBM PC 14. AOI graphics and the television commercial scene are mixed by mixer 28. A display device, i.e. monitor 27, displays the commercial shown on monitor 20 as it is overlayed by the areas of interest or boxes 10 and 12, shown in FIG. 2 at any given synchronized time. This composite image on monitor 27 is run with the AOI coordinates fixed by PC 14 and the television commercial scene gradually changing by running VCR 29, monitor 20, and camera 16. After these AOI boxes 10, 12 no longer circumscribe the same areas of interest, an "invalid" condition exists and the VCR 29 is stopped. This defines the end of the scene. If a next scene is to start at once, this time (seconds or television frames) of the current frame from the beginning of the commercial is recorded as the next scene. Then the scene is changed and the IBM PC 14 and joystick 24 are used to produce a new set of boxes (AOI's) for the next scene. This process is done by a slow motion operation of monitor 20 through a VCR 29 containing the television commercial. By the scheme shown in FIG. 14, the television commercial inputted from VCR 29 to monitor 20 can be synchronized with the superimposed boxes (AOI's) showing the areas of interest. By processing the television commercial with a system as shown in FIG. 14, the television commercial can have a real time synchronized format being a series of scenes with starting times and durations and each scene can have boundaries defined by a number of areas of interest (AOI's) outlined in accordance with any x,y coordinate format determined by an operator utilizing joystick 24 and IBM PC 14. This process creates digital information or data reducing scenes to (a) starting time or frame, (b) duration in time or frames and (c) AOI's valid during the scene. This results in a real time profile of the commercial, allowing economical further processing to obtain looking time in each AOI. This is an end result.

As so far explained, as a first step in processing the commercial, the commercial is divided into scenes with boundaries for areas of interest (AOI's) and lasting a defined time, or number of frames. Although a joystick has been suggested for the purpose of producing the areas of interest 10, 12 of a given scene S, a standard computer keyboard can be used to input the x,y coordinates of the AOI's for a scene and to adjust the coordinates on a stopped frame of any scene S as displayed on monitor 27 until the coordinates graphically define the AOI's for the scene as shown on monitor 27. When the AOI's are graphically selected, they are displayed on processing monitor 27, shown in FIG. 14. In the preferred embodiment of the invention, the AOI's are recorded in data file 126. Data file 126 contains start time and duration for each scene as well as the name and number of each AOI in each scene and the coordinates of the boundaries of each AOI box. Consequently, VCR 29 plays the television commercial and the fixed blocks (AOI's) of a selected scene S are displayed on monitor 27. As the scene changes wherein the areas of interest, AOI's 10, 12 are no longer valid, a new scene must be created. The new scene is required when the AOI's, which are fixed, are no longer valid as the television commercial, which is variable, is displayed by monitor 27. If there is a change in the audio signal within a given scene while the AOI's are valid, the scene can be changed or can be divided into various subscenes with the same areas of interest but with different audio presentations. In this manner the audio information can be correlated with video information. All of these techniques produce parameters of scenes and areas of interest (AOI's) for the individual scenes which information is synchronized with the commercial played by VCR 29 onto monitor 20, as shown in FIG. 14. This process of obtaining scenes and AOI's is one aspect of the present invention.

As shown in FIG. 2, the circles M, N and 0 have relative sizes determined by the mean percentage of time during scene S that the eyes of the several viewers were directed to the AOI's 10, 12 or, as an alternative, outside of these areas (not AOI). As can be seen, in this actual example of scene S, which had a duration of 3.8 seconds, the sample of viewers spent an average of 55.46% of the total looking time during scene S on AOI (1) or 10. This AOI is the eyes of the woman. In this example, 43.80% of the time the several viewers were looking somewhere in the lower portion of the woman's body, i.e. AOI (2) or 12. Consequently, the viewers tested in this example looked at AOI's 10, and 12, 99.26% of the time. During the scene duration of 3.8 seconds, the woman's features did not substantially change from the AOI's 10 and 12.

Figure 3:
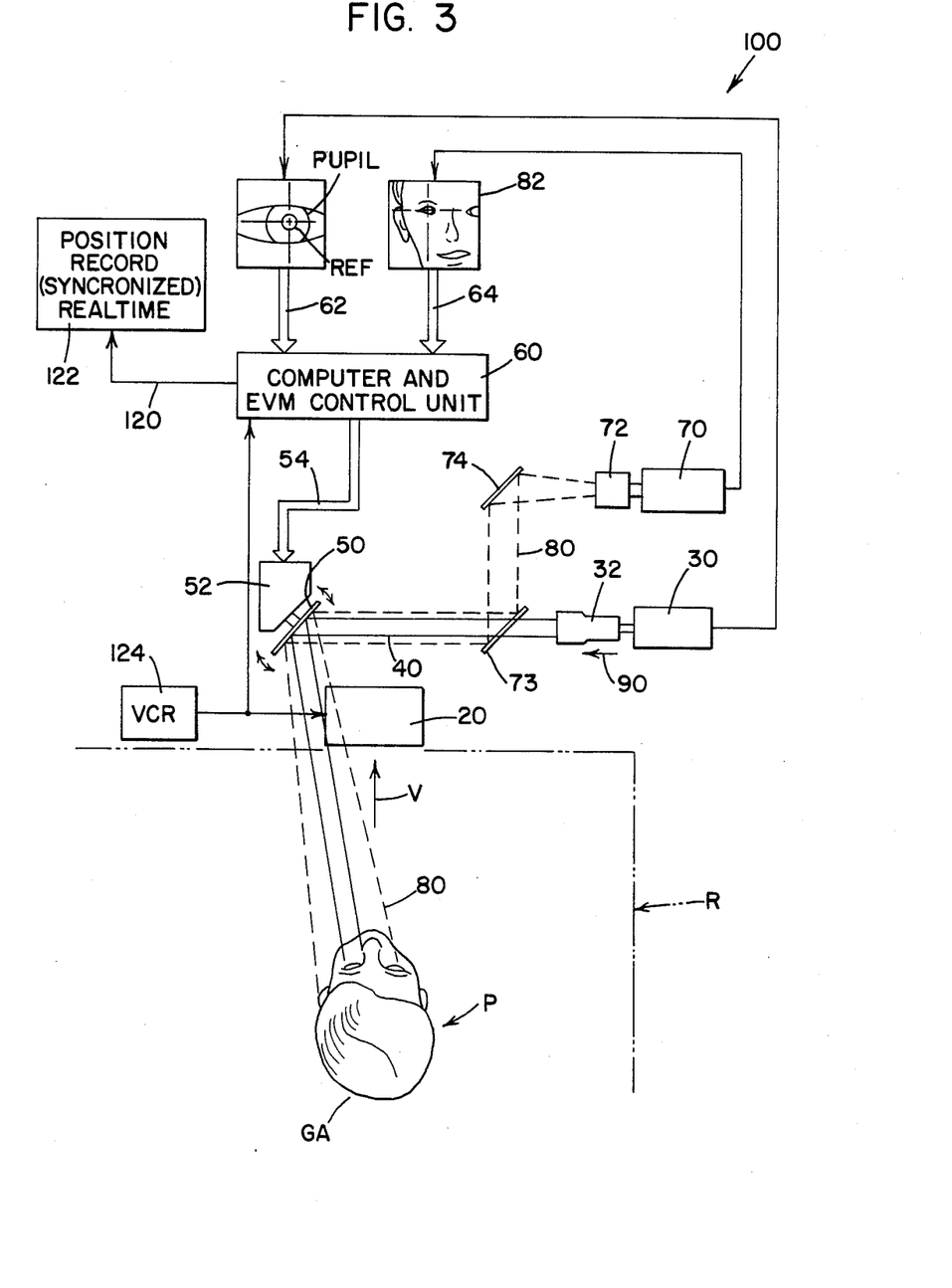
FIG. 3 is a schematic diagram of eye movement monitoring equipment employed in accordance with the preferred embodiment of the present invention and schematically illustrating a visually neutral room used in practicing the invention.
Figure 4:
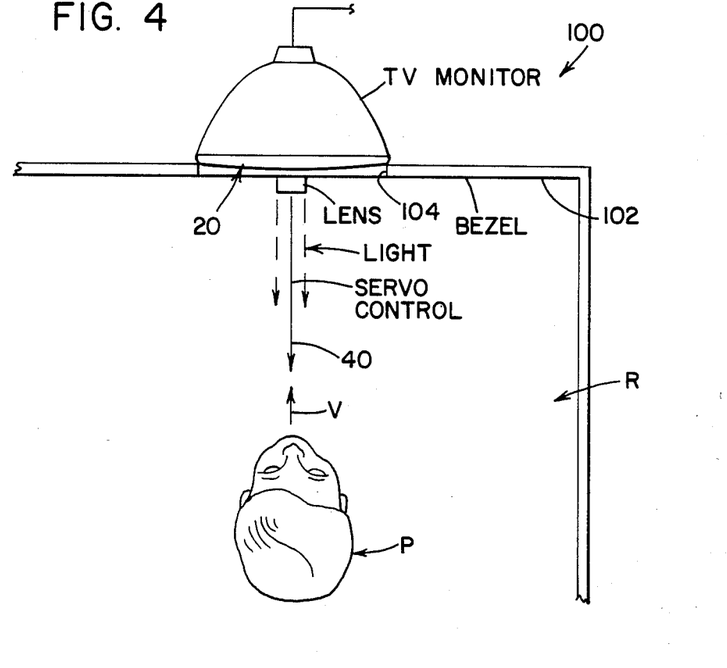
FIG. 4 is a schematic view showing the visually neutral room forming one aspect of the present invention.
Figure 5:
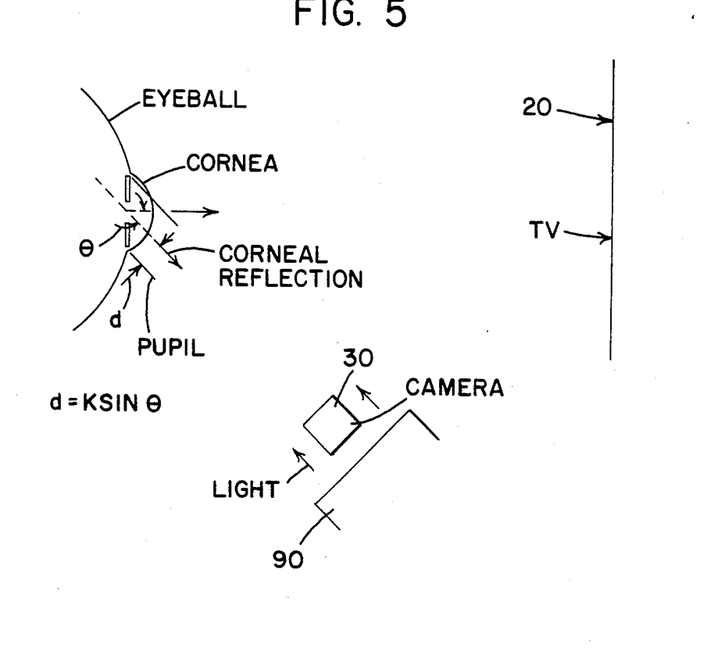
FIG. 5 is a schematic diagram illustrating a human eye and the technique for measuring and recording eye position.
Figure 6:
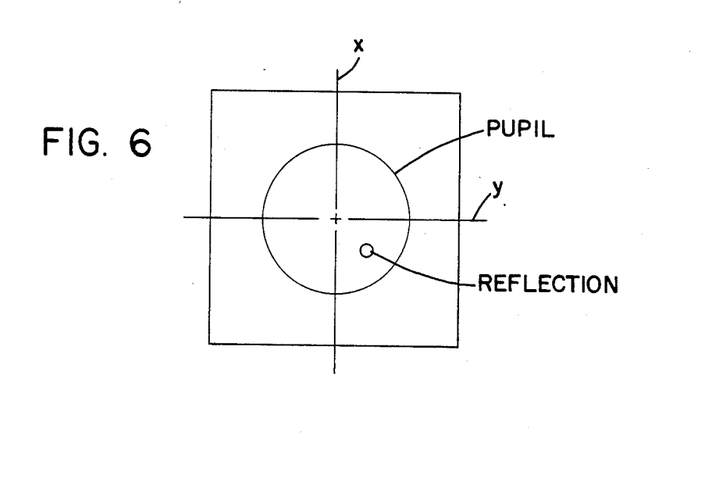
FIG. 6 is an enlarged view showing the output of the monitoring camera, shown in FIG. 5.

Referring now to FIG. 3, the preferred embodiment of the invention for recording eye movement is illustrated wherein a visually neutral room R is provided for an individual or viewer P having a line of vision V toward television monitor 20, on which the commercial being analyzed is projected. The scenes and AOI data can have been produced already or can be produced later since, in accordance with the invention, the scene data are synchronized with the commercial and have AOI's recorded as coordinates. A visually neutral room has been defined above and indicates the room wherein the individual viewing the television commercial does not have physical restraints and/or obtrusive equipment exposure. As shown in FIG. 4, the hidden equipment area 100 is behind a wall 102 defining visually neutral room R with an opening 104 through which television monitor 20 can be viewed and through which the optical equipment is aimed at the subject's eye in an unobtrusive manner. The optical equipment is an eye movement monitoring system such as model No. 1998 available from Applied Science Laboratories in Waltham, Massachusetts. This equipment includes a camera 30 with telephoto lens 32 directed in an image path 40 to the eyes of person P. Mirror 50 is controlled by servomechanism 52 movable by information in line 54 from eye view monitor 60 having data inputs 62 and 64. Input 62 is a video signal depicting the image from camera 30. This signal is processed by the EVM control unit and computer 60 to calculate the vector distance between the corneal reflection center and center of the eye pupil in accordance with standard practice. The resulting vector is used to determine eye line-of-gaze with respect to the monitor 20. This known process is schematically illustrated in FIGS. 5 and 6 wherein light source 90 projects along the same axis as the viewing axis of camera 30 to provide a bright pupil and an even brighter corneal reflection. The geometry of FIG. 5 indicates that the position of the reflection with respect to the center of the pupil is indicative of the direction in which the pupil is looking toward monitor 20.

The cornea has a different radius of curvature than the eyeball itself so that the corneal reflection and pupil displacement, by angle and distance, is indicative of the eye line-of-gaze as it is viewing the television commercial displayed on monitor 20, irrespective of head movement. A second camera 70 has a wide angle lens 72 directed toward beam splitter 73 by a fixed mirror 74. The wide angled path 80 views the total head of person P at the general area GA of room R to produce intelligence or data shown as an image 82 forming the input 64 to EVM control unit and computer 60. These image data are processed by EVM control unit and computer 60 to locate the pupil of the eye and to control mirror 50 through servo-mechanism 52 so that the pupil of the eye is within the angle of view of lens 32 for camera 30. Camera 30 is the standard eye movement camera used to measure the distance between the center of the pupil and the corneal reflection to determine the position of the eye at any given time. The eye monitoring equipment shown in FIG. 3 has, as an output from computer 60, data line 120 carrying the x,y coordinates of the eye position for viewer P at any given time. Recording station 122 is used to record, i.e. store, the position of the eye at any given time. The entire system is synchronized by vertical sync pulses, extracted by EVM control unit 60 from video cassette player 124. Vertical sync pulses occur every 1/60 second, i.e. every television field. Thus, the x,y position of the eye at each television field interval is stored on the basis of real time as subject P is viewing the television commercial being played by a video cassette player and displayed in real time by monitor 20. By recording the x,y coordinates on the basis of time, all information needed to construct saccades and fixations is obtained and stored with time basis in recorder 122. This commercial includes the series of successive scenes one of which has been explained in detail with respect to FIGS. 1 and 2.

Each scene is defined by a starting time and duration and is divided into rectangular areas of interest (AOI's) defined by the position coordinates of the sides of the rectangles. The scene and AOI data for the commercial are recorded as shown by recorder 126 in FIG. 14. The data stored in recorder 122 of FIG. 3 for an individual and the data stored in recorder 126 at FIG. 14 for a commercial are both synchronized in time with the commercial displayed on monitor 20 in FIGS. 3 and 4.

Figure 15:
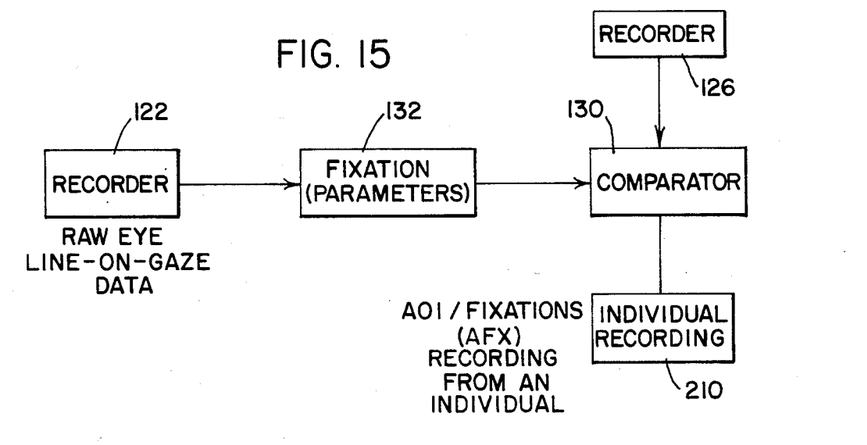

As shown schematically by box 132 in FIG. 15, the raw eye line-of-gaze data recorded by recorder 122 is reduced to a set of fixations. Each fixation is identified by parameters, i.e. starting time, duration, and x,y position coordinates. These parameters are compared to the recorded data information on the scenes and respective areas of interest in these scenes from the recorder 126 by the comparator 130. In this manner, it is possible to determine the fixations in each AOI, the fixations during each scene, the duration of the fixations in any area of interest, the percentage of fixation durations for a given area as compared with the duration of fixations for the total scene in which the area exists (i.e. percent of time spent fixating a given area), a summation of the fixation durations compared to the number of fixations in a given area or given scene (average fixation duration in an area), the number of fixations in a scene as compared to length of time of the scene, comparison of this information with other areas of interest, the number of fixations in a principal area of interest in a scene as compared to the number of principal areas of interest in a scene, the mean saccade length in degrees between fixations, the median distance in degrees between sequential fixation points and a mirade of other data generated by the manageable fixation data consisting of fixation start time, fixation duration and the x,y coordinates, or gaze position, all synchronized in time with the television commercial. As can be seen, a tremendous amount of information regarding the visual impression of each scene in a commercial may be obtained by utilizing the present invention which compares a series of scenes with defined AOI's to, in real time sense, the position of a viewer's eye at any given time as it relates to the AOI's. By this information, a tremendously versatile end product is obtained which can be employed for the purposes of evaluating any commercial on an objective basis with repeatability heretofore unobtainable.

Figure 7:
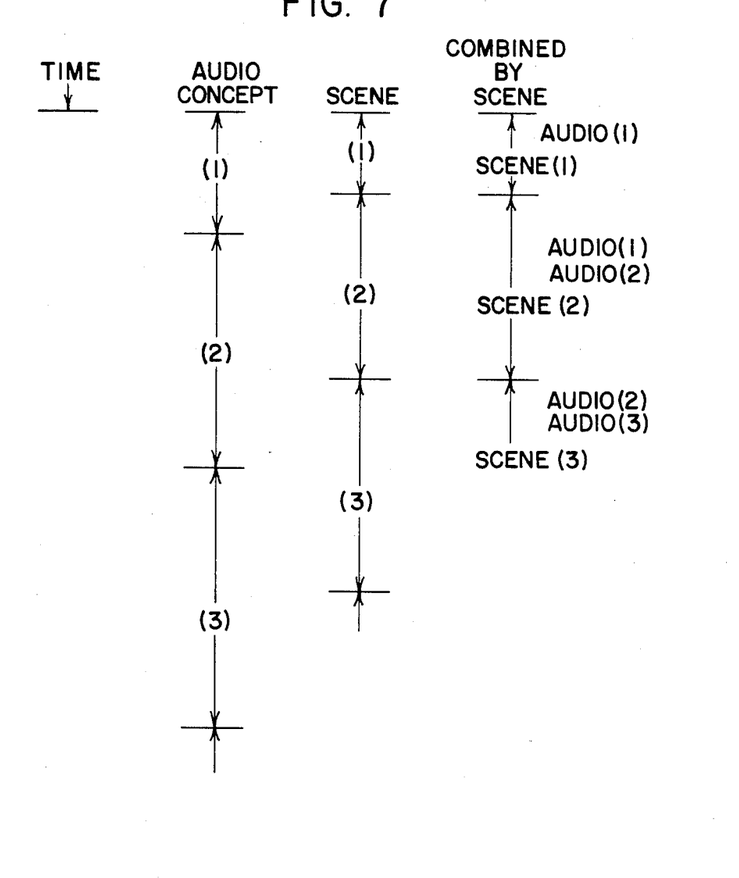
FIG. 7 is a line diagram of a television commercial showing interposed audio concepts and specific visual scenes.

Referring now to FIG. 7, a line diagram is illustrated for time which divides the scenes of a television commercial into successive times based upon the commercial itself. As can be seen the audio concept does not necessarily correlate exactly with the various visual scenes. Consequently, an analyzed scene appearing in the right column may be a period of time when the image does not change and the audio message has a certain portion of an audio concept. Each scene is defined by a start time and duration during which the image can be divided into a single set of areas of interest. A scene can also be changed when an audio change occurs as well as when a visual change has occured. The reason for this feature has been explained.

Each scene, with the lines or graphics representing area of interest boundaries, is displayed on monitor 27 as shown in FIG. 14. A still camera 140 records each successive scene. Scene start time and duration as well as area of interest boundary coordinates are recorded for each scene by the IBM PC on recorder 126.

Figure 8:
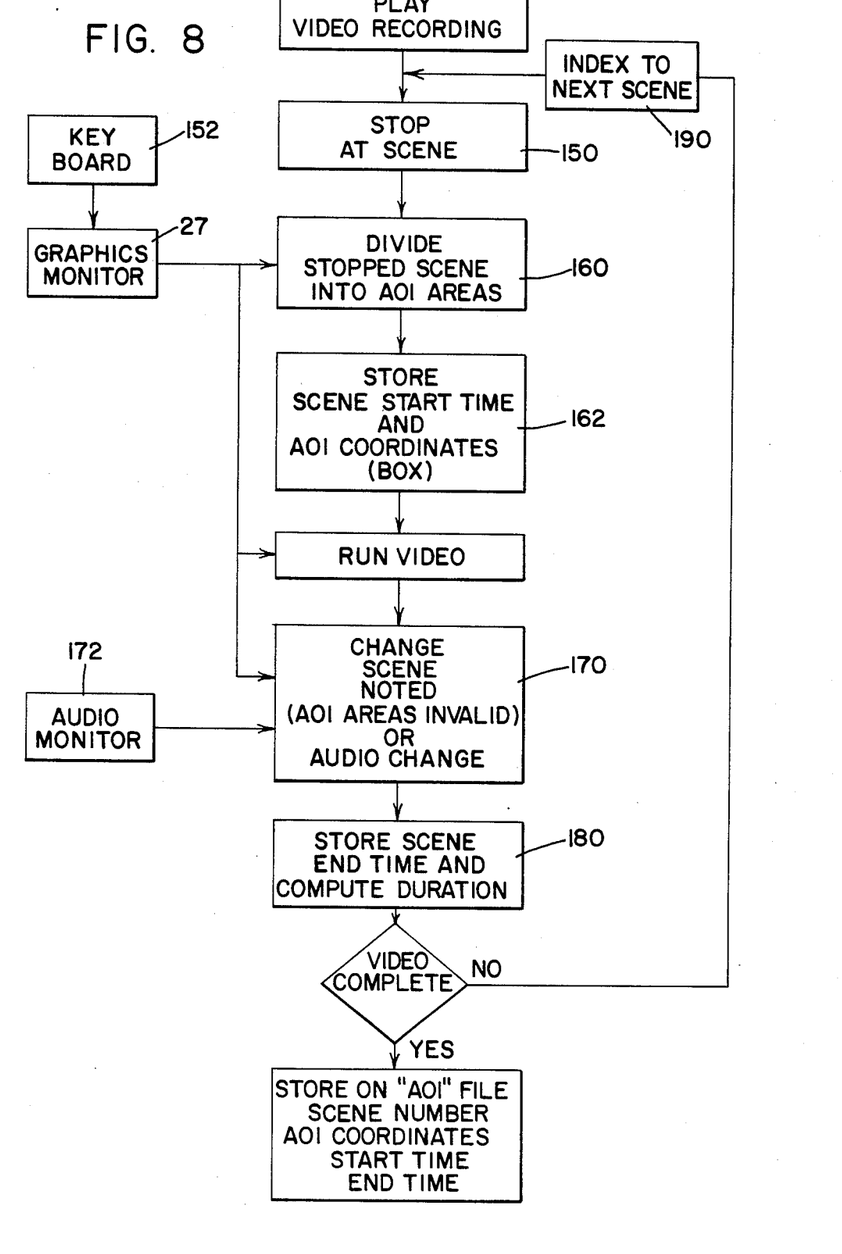
FIG. 8 is a block diagram of the preferred embodiment of the present invention.

Referring now to FIG. 8, a block diagram of the method and system used in the present invention for developing scene information as so far explained in connection with FIG. 14 is illustrated in another way. In accordance with this block diagram, the commercial is available as a video recording which is played by VCR 29. The scene is stopped as indicated by box 150. A keyboard 152 or joystick 24 is then employed to exhibit the areas of interest needed for the particular scene on monitor 27. This is indicated by box 160. Thereafter, the scene number, scene start time and scene duration together with the box coordinates, are stored such as by recorder 126 in FIG. 14. This is indicated by box 162. Still camera 140 can then take a photograph of the new scene together with the graphics dividing the scene into AOI's, such as shown in FIG. 2. Thereafter, VCR 29 is continued at any rate and display monitor 27 is watched until the graphics or AOI's so far recorded and displayed by monitor 27 are invalid. This is then the time to stop the existing scene or start a new scene as illustrated by box 170 of FIG. 8. Of course, a new scene could be created by a new sound signal from audio monitor 172, which indicates a different audio concept being transmitted with the commercial. With the new scene, a new photograph is taken by still camera 140. This is illustrated as box 180. If the video has not been completed, then the system shifts to the next scene as illustrated by box 190. If the video has been completed, then recorder 126 has stored all information available into an "AOI" file including scene members, AOI coordinates, start time for each scene, and duration or end time for each scene. All this information is stored in recorder 126 of FIG. 15 on the basis of time or frame members so that it can be synchronized with information from the eye monitor by an appropriate comparator 130.

Figure 9:
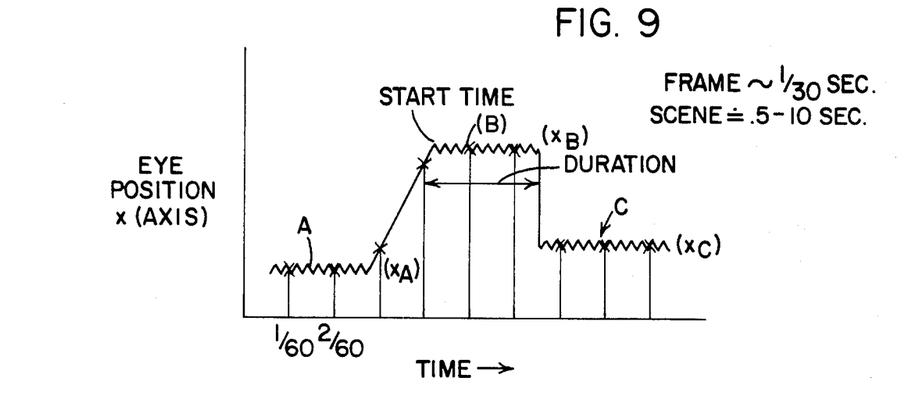
FIG. 9 is a graph illustrating the sampling technique employed in the present invention for one eye movement coordinate.
Figure 10:
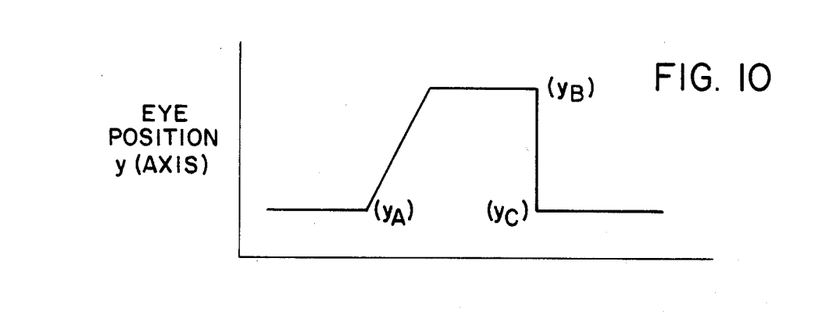
FIG. 10 is a view similar to FIG. 9 showing the other eye movement coordinate sampled in accordance with the present invention.
Figure 11:
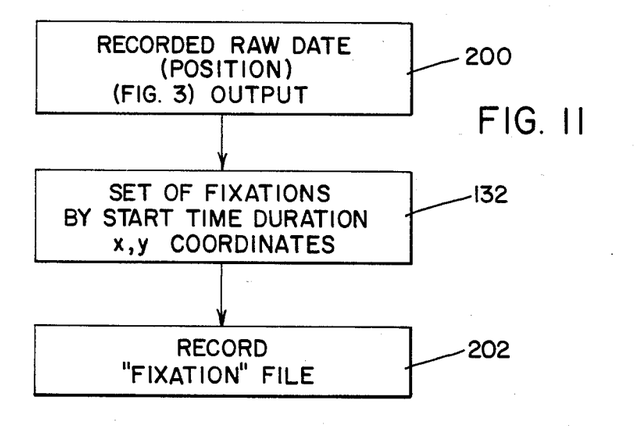
FIG. 11 is a block diagram of a further aspect of the present invention.
Figure 12:
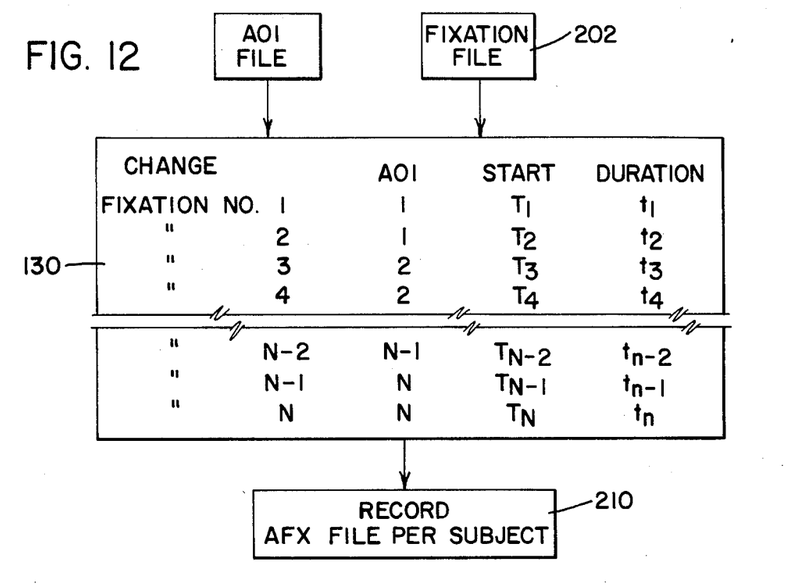
FIG. 12 is a fixation read-out obtainable from the present invention as an ultimate tool obtainable by the present invention.
Figure 13:
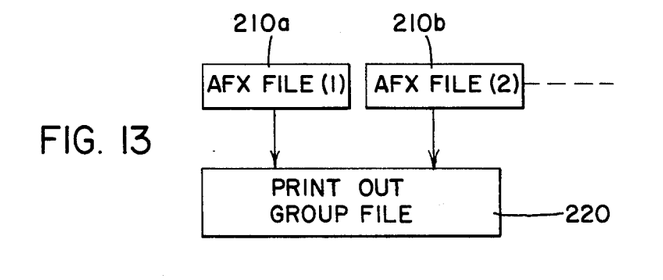
FIG. 13 is a block diagram illustrating further processing obtainable by using the present invention; and, FIG. 14 is a schematic block diagram showing the preferred embodiment of the present invention as it is now practiced.

Referring now to FIGS. 9 and 10, the graphs illustrate fixations A, B and C. These fixations are determined by the eye position at each rapidly occurring interval defined by television sync pulses, i.e. each 1/60 second. If the eye line-of-gaze does not change significantly for an appropriate number of clocked intervals, then that gaze point is identified as a fixation and the starting time of the fixations is known within a certain limit. When eye line-of-gaze does change significantly that fixation is over and thus the duration of the fixation is known. This information identifies an individual's eye fixation point at any given time during the viewing of the commercial. This fixation information is then recorded for each individual. Raw eye position data storage is shown in box 200 of FIG. 11. These are the data recorded by recorder 122, shown in FIG. 3. These raw data information on eye line-of-gaze for each individual are then reduced and converted to a set of fixations by start time, duration and x,y coordinates, such as indicated by box 132 in FIG. 11. This processed information is then recorded in a fixation file 202 for each individual which individual fixation file is compared to the single AOI file from recorder 126. Comparator 130 does this combination and creates information, such as shown in FIG. 12. As can be seen, each fixation of an individual is numbered. The area of interest containing the fixation is recorded together with the start time and duration for each fixation of each individual. All of this information relating individual fixations to areas of interest is recorded in an individual file 210 for each individual. This produces an AFX file for each individual or subject as illustrated at the output of FIG. 12. Referring now to FIG. 13, files for each individual are then averaged as indicated by block 220 having inputs 210a, 210b, etc. from each of the several persons P viewing the commercial. Print-out 220 can then be us the end product for various analysis including the distribution of looking indicated by circles M, N and 0 of FIG. 2. Also, the various other parameters determined by fixations can be obtained with the composite information.

Having thus described the invention, it is claimed:

1. A method of generating a distribution of actual looking time of a group of individuals, each viewing a television program containing a video signal and a synchronized audio signal, both signals recorded on a real time basis to form said program, said method comprising the steps of:

(a) providing a viewing room with a video monitor for display of said television program to a selected one of said individuals at a given general area of said room, a dimly visible near infrared light source shining toward said individual at said given general area in a given direction, thereby producing a reflection from the surface of the cornea of an eye of said individual, a video camera disposed so that its optical axis is coaxial with said direction of said light source and a tracking mirror servo-mechanism for directing said light source and camera towards and eye of said individual at said general area of said room with said individual not being connected to equipment in said room;

(b) displaying said television program to said individual at said general area in said room by way of said video monitor;

(c) computing the point of gaze of said eye of said individual at preselected time intervals by way of displacement of said corneal reflection from the pupil of said eye at each of said preselected time intervals while said individual is viewing said television program from said general area in said room;

(d) recording said point of gaze at each of said intervals;
(e) producing a series of successive fixation parameters specifying eye fixations including recorded starting time, duration and x, y coordinates for each successive fixation of the eye of said individual while viewing said television program;
(f) recording said series of fixations in a given first data file;
(g) previously or afterwards dividing said television program into a series of scenes having a start time and a duration and each made up of known areas of interest with a fixed set of x, y coordinates defining each boundary for each area of interest of each scene, said start times and durations being selected in accordance with the time said areas of interest are generally the same or said audio signal is presenting a given audio concept;
(h) recording said scenes by starting time, duration and fixed coordinates of areas of interest in said scenes into a second data file;
(i) comparing said first and second data files for said individual to produce a third data file containing specific fixations in each area of interest in each scene of said combined video and audio television program;
(j) repeating said steps for a number of individuals; and,
(k) producing a compilation chart specifying the distribution of looking time in all areas of interest in each scene for said number of individuals.

2. A method of measuring and recording eye point of gaze and describing these data as a set of eye fixations on a television program containing a video signal and a synchronized audio signal, both signals recorded for real time display on a plane with x, y axis, said method comprising the steps of:
(a) providing a visually neutral room with a video monitor for displaying said television commercial to a selected individual seated at a given general area of said room and facing said monitor, a barely visible near infrared light source shining in a given direction toward said individual, a hidden eye monitor camera disposed coaxially with said direction of said light source and a tracking mirror servomechanism for directing said light source and camera toward the pupil of an eye of said individual whereby said individual cannot perceive said camera or mirror nor need said individual be connected to equipment in said visually neutral room;
(b) displaying said television program to said individual at said general area in said room by way of said video monitor;
(c) computing the point of gaze of said eye of said individual at preselected time intervals by way of said eye monitor, said intervals being substantially less than 1/30 second;
(d) reducing said eye point of gaze data into a series of fixations having a starting time, duration and x, y coordinates in said video display; and,
(e) recording said fixations in a storage file as a set of eye fixations synchronized with said video and audio signals.

3. A method as defined in claim 2, wherein said intervals are about 1/60 second.

4. A method of generating a distribution of actual looking time of a group of individuals each viewing a television program containing a video signal and a synchronized audio signal, both signals recorded for real time display on a plane with x, y axes, said method comprising the steps of:
(a) displaying said television program to an individual at a general area in a visually neutral room by way of a video monitor in said room;
(b) computing the point of gaze of said eye of said individual at a preselected time intervals by way of an Eye view Monitor, said intervals being substantially less than about 1/30 second by the corneal reflection, pupil referenced eye monitor technique;
(c) reducing said eye point of gaze data into a series of fixations having a starting time, duration and x, y coordinates in said video display; and,
(d) recording said fixations in a storage file as a set of eye fixations synchronized with said audio and video signals.

5. A method as defined in claim 4, including the further steps of:
(e) dividing said television program into a series of scenes each having a time duration and each made up of known areas of interest with a fixed set of x, y coordinates for each area of interest of each scene;
(f) recording the starting time and duration of said scenes with said start time and duration being selected as the time said areas of interest are generally the same or said audio signal is competing a given audio concept;
(g) recording said scenes by starting time, duration and fixed coordinates of areas of interest in said scenes into a first data file;
(h) comparing said fixation storage file and said first data file for said individual to produce a second data file containing specific fixations in each area of interest in each scene of said combined video and audio program;
(i) repeating said steps for a number of individuals; and,
(j) producing a compilation chart specifying the distribution of looking time in all areas of interest in each scene for said number of individuals.

6. A method of generating a distribution of actual looking time of a group of individuals each viewing a television program containing a video signal and a synchronized audio signal, both signals recorded for real time display on a plane with x, y axes, said method comprising the steps of:
(a) displaying said television program to an individual at a general area in a visually neutral room by way of a video monitor in said room;
(b) computing the point of gaze of said eye of said selected individual at preselected time intervals by way of an Eye View Monitor, said intervals being substantially less than about 1/30 second by the corneal reflection, pupil references eye monitor technique;
(c) reducing said eye point of gaze data into a series of fixations having a starting time, duration and x, y coordinates in said video display; and,
(d) recording said fixations in a storage file as a set of eye fixations synchronized with said television program;
(e) displaying said television program at a variable rate different from said real time on a synchronizable display device;
(f) providing a device for dividing said displayed program into selected areas of interest and displaying the boundaries of said areas of lines superimposed over the television program on said synchronizable display device;

(g) recording a scene synchronized starting time when a given selected scene of said program is displayed on said projecting device;

(h) recording the x, y coordinates of said boundaries of said areas displayed on said display device for each area of interest in said scene;

(i) recording said synchronized starting time for said scene and the coordinates of said areas of interest of said scene;

(j) continuing said program at said variable rate on said synchronizable projecting device until said areas of interest are no longer valid;

(k) recording the difference between the scene starting time and the synchronized time when said areas of interest are no longer valid as the duration of said scene;

(l) recording said scene as a starting time, duration and set of coordinates defining said areas of interest;

(m) recording a next adjacent scene at the end of the prior mentioned scene;

(n) repeating steps (g) through (m) until the total television program has been divided into scenes and areas of interest in said scenes;

(o) recording said scenes by starting time, duration and fixed coordinates of areas of interest in said scenes into a first data file;

(p) comparing said fixation file for said individual and said first data file for said television program to produce a second data file containing specific fixations in each area of interest in each scene of said television program;

(q) repeating the steps for a number of individuals using the same data file.

* * * * *